US009925075B2

(12) United States Patent
Mitsudo et al.

(10) Patent No.: US 9,925,075 B2
(45) Date of Patent: Mar. 27, 2018

(54) STENT

(75) Inventors: Kazuaki Mitsudo, Kurashiki (JP); Koji Akimoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 35 days.

(21) Appl. No.: 14/349,439

(22) PCT Filed: Aug. 22, 2012

(86) PCT No.: PCT/JP2012/005248
§ 371 (c)(1),
(2), (4) Date: Jul. 7, 2014

(87) PCT Pub. No.: WO2013/065218
PCT Pub. Date: May 10, 2013

(65) Prior Publication Data
US 2014/0358218 A1    Dec. 4, 2014

(30) Foreign Application Priority Data
Nov. 2, 2011    (JP) .................................. 2011-241306

(51) Int. Cl.
*A61F 2/915*    (2013.01)

(52) U.S. Cl.
CPC ...... *A61F 2/915* (2013.01); *A61F 2002/9155* (2013.01); *A61F 2002/91575* (2013.01);
(Continued)

(58) Field of Classification Search
CPC .............. A61F 2/915; A61F 2002/9155; A61F 2002/91575; A61F 2250/0071;
(Continued)

(56) References Cited

U.S. PATENT DOCUMENTS 5,913,897 A * 6/1999 Corso, Jr. ................. A61F 2/91
                                                  623/1.15
6,042,597 A * 3/2000 Kveen ...................... A61F 2/91
                                                  623/1.15
(Continued)

FOREIGN PATENT DOCUMENTS

EP    1 034 751 A2    9/2000
EP    1 782 766 A2    5/2007
(Continued)

OTHER PUBLICATIONS

International Preliminary Report on Patentability issued in International Application No. PCT/JP2012/005248 dated May 6, 2014.
(Continued)

*Primary Examiner* — Katherine Rodjom
(74) *Attorney, Agent, or Firm* — Oliff PLC

(57) ABSTRACT

Provided is a stent of a novel structure with which deflection of a line-shaped body during expansion is prevented and a substantially uniform expansion is achieved over an entire length thereof, and with which, after implantation, stent fracture and damage of body tissue can be prevented by the stent exhibiting a superior pliability and conformability to a shape of a somatic lumen. A stent having a cylindrical peripheral wall formed with a line-shaped body that extends in a helical form in a circumferential direction while reciprocating in an axial direction at a given amplitude. In the stent, connecting parts are formed to link portions of the line-shaped body that are adjacent in the axial direction, and a friable part is provided to rupture itself by being implanted in the somatic lumen and release a link made by the connecting parts.

20 Claims, 7 Drawing Sheets

(52) U.S. Cl.
CPC ............... *A61F 2210/0004* (2013.01); *A61F 2230/0054* (2013.01); *A61F 2230/0091* (2013.01); *A61F 2250/0071* (2013.01)

(58) Field of Classification Search
CPC ...... A61F 2230/0054; A61F 2230/0091; A61F 2210/0004
See application file for complete search history.

(56) References Cited

U.S. PATENT DOCUMENTS

| | | | |
|---|---|---|---|
| 6,423,091 B1* | 7/2002 | Hojeibane | A61F 2/88 623/1.15 |
| 7,029,492 B1 | 4/2006 | Mitsudou et al. | |
| 7,329,276 B2* | 2/2008 | Smith | A61F 2/91 623/1.16 |
| 8,500,793 B2* | 8/2013 | Zipse | A61F 2/91 623/1.2 |
| 8,870,940 B2 | 10/2014 | Venturelli et al. | |
| 2005/0125051 A1* | 6/2005 | Eidenschink | A61F 2/91 623/1.12 |
| 2006/0064155 A1* | 3/2006 | Bales | A61F 2/91 623/1.15 |
| 2006/0235505 A1 | 10/2006 | Oepen et al. | |
| 2006/0248698 A1 | 11/2006 | Hanson et al. | |
| 2008/0177376 A1 | 7/2008 | Krivoruchko et al. | |
| 2008/0215129 A1 | 9/2008 | Venturelli et al. | |
| 2008/0306583 A1* | 12/2008 | Bashiri | A61F 2/91 623/1.18 |
| 2008/0319529 A1 | 12/2008 | Krivoruchko et al. | |
| 2008/0319534 A1 | 12/2008 | Birdsall et al. | |
| 2010/0057190 A1 | 3/2010 | Issenmann | |
| 2010/0249904 A1 | 9/2010 | Takayuki et al. | |
| 2011/0060401 A1* | 3/2011 | Hoerstrup | A61F 2/2418 623/1.16 |
| 2011/0125251 A1* | 5/2011 | Cottone | A61F 2/88 623/1.16 |
| 2011/0218614 A1 | 9/2011 | Lam | |

FOREIGN PATENT DOCUMENTS

| | | |
|---|---|---|
| JP | U-4-126558 | 11/1992 |
| JP | A-2000-316983 | 11/2000 |
| JP | A-2002-52086 | 2/2002 |
| JP | 2008-511424 A | 4/2008 |
| JP | A-2008-539889 | 11/2008 |
| JP | 2009-502307 A | 1/2009 |
| JP | A-2009-82245 | 4/2009 |
| JP | A-2010-516340 | 5/2010 |
| JP | A-2011-502636 | 1/2011 |
| WO | 2006/026778 A2 | 3/2006 |

OTHER PUBLICATIONS

International Search Report issued in International Patent Application No. PCT/JP2012/005248 dated Sep. 25, 2012.
Apr. 30, 2015 European Search Report issued in European Patent Application No. 12846004.5.
Jun. 1, 2015 Office Action issued in Chinese Application No. 201280053289.2.
Jan. 14, 2016 Office Action issued in Japanese Patent Application No. 2013-541594.
Aug. 22, 2016 Office Action issued in Japanese Patent Application No. 2013-541594.
Feb. 16, 2017 Office Action issued in Japanese Patent Application No. 2013-541594.

\* cited by examiner

＃ STENT

TECHNICAL FIELD

The present invention relates to a medical stent to be used, for example, to keep the inner diameter of the somatic lumen in an expanded state by being expanded and implanted within the somatic lumen such as blood vessels.

BACKGROUND ART

Conventionally, a stent has been used in the percutaneous transluminal coronary angioplasty (PTCA), for example, to prevent a stenosis portion of the coronary artery from restenosis due to recoil or the like after dilation with a balloon. The stent has a peripheral wall portion in an approximate shape of a cylinder, for example, and this peripheral wall portion is composed of a line-shaped body that extends in a helical form in the circumferential direction while reciprocating in the axial direction at a given amplitude. Then, the stent inserted into the somatic lumen such as the coronary artery under a constricted condition in the radial direction is expanded in the radial direction with a balloon or by self-expansion using the shape-memory effect of the stent itself to be implanted in close contact with the inner wall surface of the somatic lumen. This prevents restenosis caused by recoiling and the like due to the stent's rigidity in the radial direction, thus maintaining the inner diameter of the somatic lumen in a state of being expanded with a balloon.

Meanwhile, in the stent formed by coiling the line-shaped body in a helical form, since the portions adjacent to each other in the axial direction are not positioned against each other allowing them to move freely in the axial direction, there is a risk of not expanding uniformly due to the density disparity in the arrangement of the line-shaped body when the stent is expanded in the radial direction with a balloon and the like. Therefore, in Japanese Domestic Publication of International Patent Application No. JP-A-2011-502636 (Patent Document 1) proposes a structure where a connecting part (connector 30) is provided to link the adjacent portions of the line-shaped body to each other in the axial direction. This allows the rigidity of the stent in the longitudinal direction to be enhanced to achieve configuration stability.

However, once the line-shaped body is linked by the connecting part in the axial direction, the stent's rigidity not only in the longitudinal direction but also in the radial direction is increased so that its conformability to the bend of the somatic lumen and the like is degraded. As a result, there was a risk of encountering stent fracture caused by the stent remaining in the bent portion for a long time to be charged with repeated loads of blood flow and the like, which caused a problem such as a higher rate of restenosis of the somatic lumen. In addition, as the stent's rigidity increases, the stent remaining in place gets less susceptible to deformation in conformity to the configuration of the somatic lumen, which poses another risk of damaging the body tissues such as those of blood-vessel walls by pressing the tip end of the stent against them.

BACKGROUND ART DOCUMENT

Patent Document

Patent Document 1: JP-A-2011-502636

SUMMARY OF THE INVENTION

Problem the Invention Attempts to Solve

The present invention was made against the background described above and the problems to be solved are to provide a stent of a novel structure with which deflection of the line-shaped body during expansion is prevented and a substantially uniform expansion is achieved over the entire length thereof, and with which, after implantation, stent fracture and any damage to the body tissues can be prevented by the stent exhibiting a superior pliability and conformability to the shape of the somatic lumen.

Means for Solving the Problem

In other words, a first aspect of the present invention provides a stent comprising a cylindrical peripheral wall formed with a line-shaped body that extends in a helical form in a circumferential direction while reciprocating in an axial direction at a given amplitude, the stent being characterized in that at least one connecting part is formed to link portions of the line-shaped body adjacent in the axial direction, and a friable part is provided to rupture itself by being implanted in a somatic lumen and release a link made by the connecting part.

In the stent with the structure according to the first aspect, relative movement in the axial direction of adjacent portions of the line-shaped body in the axial direction can be limited because of the connecting parts provided therein, thus restricting density disparity in the axial direction due to deflection of the line-shaped body. Therefore, the stent is expanded stably to its intended configuration when the expansion (diameter enlarging deformation) is undertaken by means of dilation with a balloon or by shape recoverability based on the shape-memory effect and the like, thus preventing any rigidity disparity or partially failed dilation caused by deflection of the line-shaped body.

Furthermore, the links made by the connecting parts are released by the friable parts that are ruptured by implantation of the stent in the somatic lumen, and after the rupture of the friable parts, adjacent portions in the axial direction of the line-shaped body is allowed to move relative to each other in the axial direction to cancel any increase in the rigidity caused by provision of the connecting parts. This enhances the conformability of the stent to the curvature of the somatic lumen so that any stent fracture (buckling of the stent) and other failures such as restenosis of the somatic lumen caused thereby is prevented from occurring, while preventing any damage to the body tissues due to the contact against the end tip of the stent.

The friable parts can be composed entirely of the connecting parts, or can be provided partially with the connecting parts. Also, the friable parts are ruptured not only by the stress acting on the connecting parts due to curving deformation of the somatic lumen caused by changes in the body posture or the pulsation of the blood vessel and the like in the somatic lumen after implantation in the somatic lumen, but also by the stress acting on the friable parts due to the expansion of the stent to the implanted condition, and these friable parts are ruptured upon or after the implantation in the somatic lumen. In addition, the friable parts are formed not only as parts with low mechanical strength but also parts that chemically rupture itself. In other words, it is possible to form friable parts using biodegradation or some materials susceptible to degradation over time.

A second aspect of the present invention provides the stent according to the first aspect, wherein the friable part is configured by making a cross sectional area extending perpendicular to a direction of linking of the connecting part smaller than that extending perpendicular to a length direction of the line-shaped body.

According to the second aspect, the friable parts are configured by making the cross sectional area of the connecting parts smaller than that of the line-shaped body, and concentrated stresses act on the friable parts upon implantation (after dilation) and after implantation of the stent allowing the friable parts to be ruptured in a stable manner. Therefore, pliability of the stent is achieved by the rupture of the friable parts, thus avoiding failures such as occurrence of stent fracture and any damage to the body tissues caused by the contact therewith.

A third aspect of the present invention provides the stent according to the first or second aspect, wherein a reciprocation amplitude of the line-shaped body in the axial direction is made approximately constant over an entire length thereof.

According to the third aspect, since the entire stent is expanded uniformly during expansion thereof, deflection of the line-shaped body in the circumferential direction is restricted. Therefore, nonuniform strain is hard to be caused during stent expansion to allow intended configuration of the stent to be obtained after expansion, while the action of concentrated stresses due to the rigidity disparity can be prevented, thus maintaining the durability of the stent.

A fourth aspect of the present invention provides the stent according to the first or second aspect, wherein a helical inclination angle of the line-shaped body relative to the axial direction is made to gradually increase toward each end of the stent to get close to a vertical angle.

According to the fourth aspect, when the stent passes through a bent portion of the blood vessel, for example, significant deformation of the tip end of the stent in the axial direction floating up toward the outer periphery can be prevented effectively. Also, since there is no need for locally providing any portion with an excessively long or excessively short amplitude in the line-shaped body, favorable effects of extension and flexion can be exerted by a stent over the entire length thereof.

A fifth aspect of the present invention provides the stent according to any one of the first to fourth aspects, wherein the at least one connecting part comprises a plurality of connecting parts formed in the length direction of the line-shaped body, and the friable part is provided in the connecting parts located in a middle section of the line-shaped body in the length direction, whereas no friable part is provided in the connecting parts located at each end of the line-shaped body in the length direction, keeping the stent in a linked state after implantation in the somatic lumen.

According to the fifth aspect, since the connecting parts are provided in a linked state all the way through in the axial direction during expansion of the stent, adjacent portions of the line-shaped body in the axial direction are relatively positioned to each other to some extent, which prevents deflection of the line-shaped body in the axial direction to have the stent expanded to its intended configuration. Also, once the stent is implanted in the somatic lumen, the friable parts are ruptured at the connecting parts located in the middle section of the line-shaped body in the length direction, which enhances the stent's pliability. Meanwhile, in an implanted state, the stent is prevented from being subject to deformation more than necessary by keeping the connecting parts located at each end of the line-shaped body in the length direction in a linked state so that the implanted stent is stably positioned in place in the somatic lumen.

A sixth aspect of the present invention provides the stent according to any one of the first to fifth aspects, wherein the connecting parts are provided at a constant interval.

According to the sixth aspect, since portions with locally higher rigidity due to the formation of the connecting parts are arranged in a uniform manner, the stent is prevented from being subject to strain deformation during expansion, thus making it possible to stably obtain the intended configuration of the stent after expansion thereof.

A seventh aspect of the present invention provides the stent according to any one of the first to sixth aspects, wherein the friable part is formed by having the portions of the line-shaped body adjacent in the axial direction welded to each other by laser.

According to the seventh aspect, the friable parts can be easily formed only at given positions by laser welding. In addition, since the thickness, width and cross sectional area and the like of the friable parts can be easily adjusted by means of controlling the duration and intensity of the laser irradiation, it is possible to control the rupture timing of the friable parts.

An eighth aspect of the present invention provides the stent according to the seventh aspect, wherein proximal protrusions are provided in the portions of the line-shaped body adjacent in the axial direction where the friable part is formed by welding the proximal protrusions to each other by laser.

According to the eighth aspect, parts to be welded by laser can be identified more easily by providing the proximal protrusions in advance on the line-shaped body. In addition, linking by laser welding is made easier by providing the proximal protrusions protruding in the direction of getting closer to each other.

A ninth aspect of the present invention provides the stent according to any one of the first to eighth aspects, wherein each end of the line-shaped body in the length direction constitutes a widened disc portion.

According to the ninth aspect, by means of providing the disc portion at each end of the line-shaped body that turns out to be a free end, problems such as damaging the body tissues by either end of the line-shaped body stuck in the somatic lumen can be avoided. Also, during angiography, both end positions of the stent in the axial direction are made visually more identifiable due to each broad disc portion working as a marker, thus making it easier to recognize the position and conditions of the stent within the somatic lumen.

A tenth aspect of the present invention provides the stent according to any one of the first to ninth aspects, wherein an adherend made of a different material is adhered to the line-shaped body, and the connecting part having the friable part is formed by the adherend.

As evident from the tenth aspect, the friable parts are not necessarily limited to those integrally formed with the line-shaped body, but can be provided by adhering thereto an adherend formed with synthetic resin, for example, integrally with the line-shaped body or adhering separately therefrom upon or after the formation thereof.

An eleventh aspect of the present invention provides the stent according to the tenth aspect, wherein the adherend is formed with a biodegradable resin.

According to the eleventh aspect, since the adherent formed with a biodegradable resin is degraded in the body after the implantation of the stent, the linking of the line-shaped body at the connecting parts are easily and surely released, thus avoiding any problems occurring such as stent fracture.

EFFECT OF THE INVENTION

According to the present invention, the line-shaped body extends in a helical form along the circumference while reciprocating in the axial direction at a given amplitude, whereas between the portions of the line-shaped body adjacent to each other in the axial direction, connecting parts are provided to link those adjacent portions to each other. This enhances the stent's configuration stability and prevents the line-shaped body from deflecting in the axial direction during expansion to cause the stent to undergo strain deformation. Furthermore, since the friable parts are provided that release the links at the connecting parts after being ruptured due to the implantation of the stent in the somatic lumen, if conformability of the stent to the shape of the somatic lumen is required, the pliability of the stent is enhanced by the rupture of the friable parts, thus enhancing the conformability of the stent to the shape of the somatic lumen. This prevents occurrence of stent fracture as well as damage, infections or the like to the body tissues caused by the somatic lumen being restricted by the stent.

EMBODIMENTS FOR CARRYING OUT THE INVENTION

Figure 1:
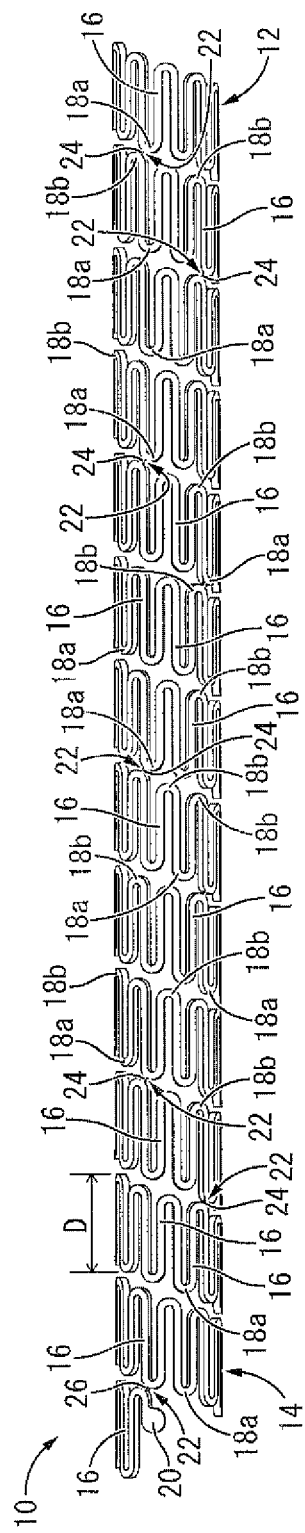
FIG. 1 is a side view of a stent as a first embodiment of the present invention.
Figure 2:
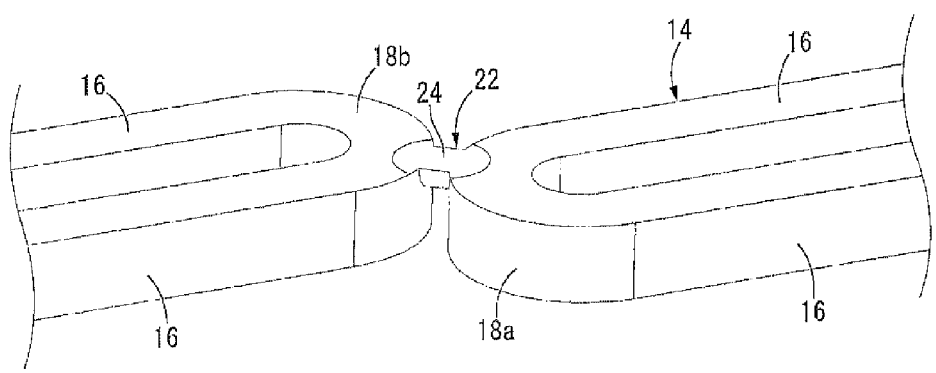
FIG. 2 is a perspective view of a key portion of the stent shown in FIG. 1.
Figure 3:
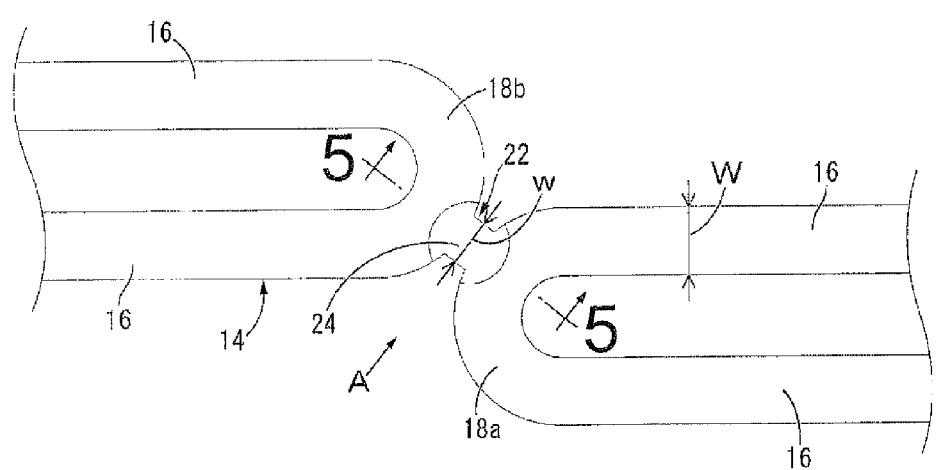
FIG. 3 is a plan view of the key portion of the stent shown in FIG. 2.
Figure 4:
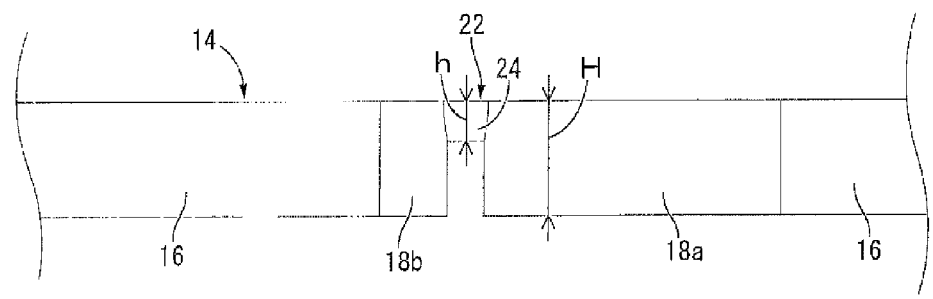
FIG. 4 is an arrow view A in FIG. 3.
Figure 5:
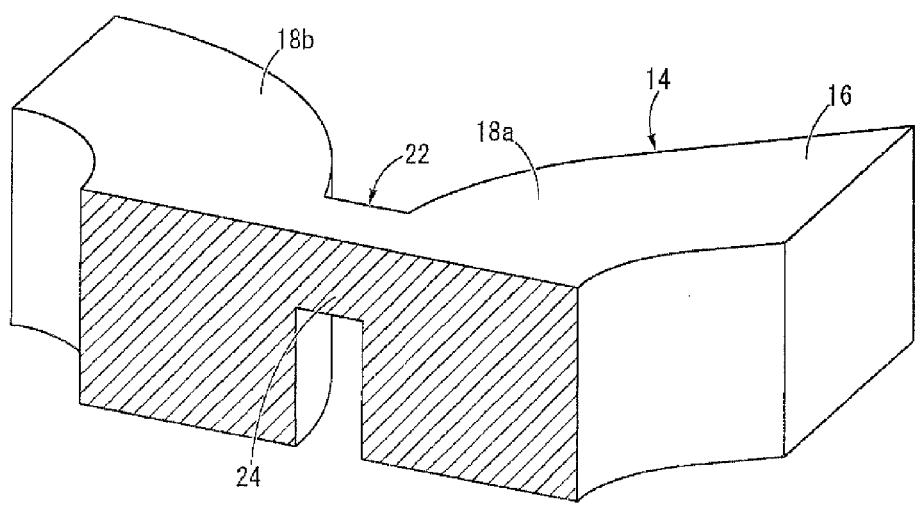
FIG. 5 is a cross sectional view taken along line 5-5 of FIG. 3.
Figure 6:
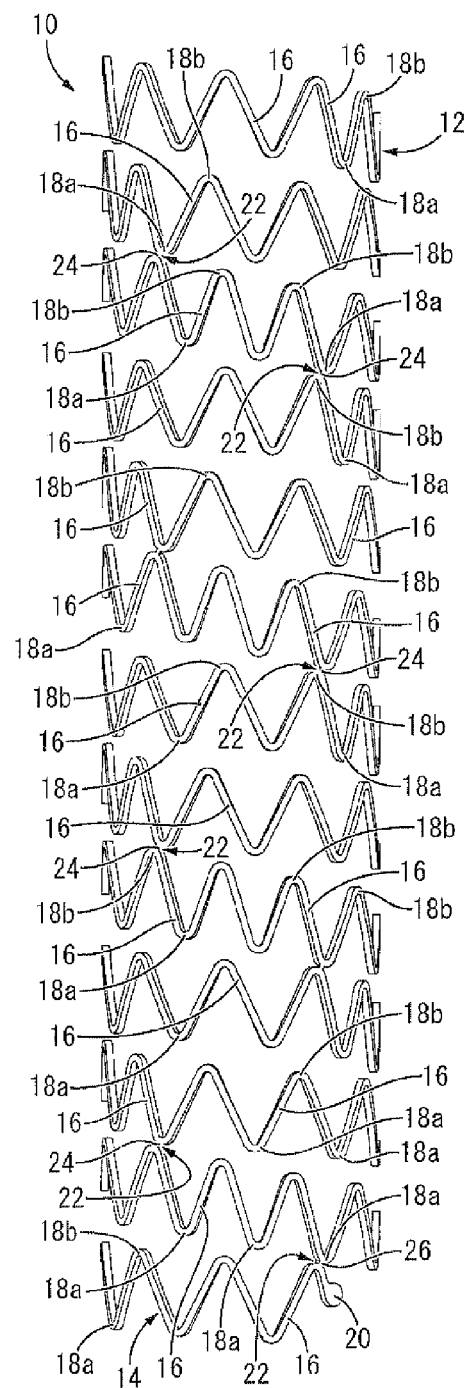
FIG. 6 is a side view showing a shape of the stent of FIG. 1 after expansion.

Embodiments of the present invention will be described in reference to the drawings as follows:

FIG. 1 shows a stent 10 as a first embodiment of the present invention. The stent 10 is provided with a peripheral wall 12 in an approximate shape of a circular cylinder over the entire length thereof, the peripheral wall 12 being formed with a line-shaped body 14. In FIG. 6 to be explained later and FIG. 1, a part of the stent 10 on the front surface side is illustrated, while the rear side thereof is omitted for better understanding. In the following descriptions, the word "axial direction" generally means the left-right direction in FIG. 1, which is the central axis direction of the peripheral wall 12.

More specifically, the line-shaped body 14 is a longitudinal member extending with a cross section of an approximate rectangle that can be formed with a biodegradable resin, synthetic resin and the like, but is preferably formed with metal materials with superior biocompatibility such as stainless steel, cobalt-chrome alloy, Ni—Ti alloy and the like (i.e. bioinert metals with no toxicity to living tissues). Also, the line-shaped body 14 extends in a helical form in the circumferential direction, in which a linear part 16 that extends in the axial direction for a given length and a curved part 18a/18b that curves approximately in a semi-circular shape are provided alternately in a continuous manner, making wave forms by reciprocating in the axial direction at a given amplitude. For the sake of explanation, the curved part with its convex facing one direction (leftward in FIG. 1) and the curved part with its convex facing the other direction (rightward in FIG. 1) are distinguished by labelling them 18a and 18b, respectively.

Especially in the present embodiment, the reciprocation amplitude of the line-shaped body 14 is made approximately constant over the entire length thereof, making uniform wave forms nearly all across the peripheral wall 12. By having the line-shaped body 14 extend in a helical form in the circumferential direction while reciprocating in the axial direction, a band-shaped body is formed extending in a helical form in the circumferential direction with a width corresponding to the amplitude of the line-shaped body 14, and the band-shaped bodies (curved parts 18a, 18b) arranged adjacent to each other in the axial direction are separated at a given distance in the axial direction. The distance D in the axial direction (see FIG. 1) from the outer peripheral apex of the curved part 18a to the outer peripheral apex of the curved part 18b of this band-like body is preferably set at 0.5 mm≤D≤2.0 mm, and more preferably at 0.9 mm≤D≤1.5 mm.

Thus, by having the line-shaped body 14 extend in a helical form in the circumferential direction while reciprocating in the axial direction at a given amplitude, the peripheral wall 12 is formed in an approximate shape of a circular cylinder over the entire length thereof. As described above, since the line-shaped body 14 extends in a helical form in the circumferential direction while reciprocating in the axial direction at a nearly constant amplitude over the entire length thereof, as shown in FIG. 1, each end of the peripheral wall 12 in the axial direction is located on a plane that extends at an angle to the axis-perpendicular direction. In summary, the peripheral wall 12 is made in a shape of a circular cylinder with each end cut off by an inclined plane. The peripheral wall 12 can be obtained, for example, by forming the line-shaped body 14 in a given configuration by means of cutting out from a metal member in an approximate shape of a cylinder by laser.

Also, each end of the line-shaped body 14 in the length direction constitutes a disc portion 20 in an approximate form of a circular disc partially widened compared to the middle section. FIG. 1 shows the disc portion 20 at one end of the line-shaped body 14, but the same disc portion 20 is also provided at the other unillustrated end.

Also, the line-shaped body 14 is provided with a plurality of connecting parts 22 in the length direction. These connecting parts 22 are provided so as to link the curved parts 18a and 18b adjacent in the axial direction to each other, each formed per a given number of curved parts 18a, and particularly in the present embodiment, each connecting part 22 is provided for every six curved parts 18a, This allows the plurality of connecting parts 22 to be provided uniformly at a nearly constant interval in the length direction of the line-shaped body 14.

More specifically, a friable part 24 is provided in the connecting part 22 located in the middle section of the line-shaped body 14 in the length direction. The friable part 24 is a part with less mechanical strength than the line-shaped body 14, and in the present embodiment, each connecting part 22 located in the middle section in the length direction is entirely composed of the friable part 24. Also, as shown in FIGS. 2 to 5, the friable part 24 is provided between the parts adjacent to each other in the axial direction (curved parts 18a, 18b adjacent to each other in the axial direction), and these curved parts 18a, 18b are linked to each other by the friable part 24. The curved parts 18a, 18b adjacent to each other in the axial direction are arranged to shift from each other in the circumferential direction so that the direction of linking of the curved parts 18a, 18b by the friable part 24 is tilted against the axial direction. However, in cases where the curved parts 18a, 18b adjacent to each other in the axial direction are aligned with each other in the circumferential direction, for example, the direction of linking of the curved parts 18a, 18b by the friable part 24 does not have to be tilted against the axial direction, but instead can be parallel to the axial direction.

Furthermore, in the present embodiment, the friable part 24 is formed by having the curved parts 18a, 18b adjacent to each other in the axial direction in the line-shaped body 14 welded to each other by laser. This allows the friable part 24 to be formed easily by after-processing, while making it possible to form the friable part 24 in any shape and size by means of properly controlling the duration and intensity of laser irradiation, thus enabling to easily control the rupture timing of the friable part 24.

Moreover, the width w of the friable part 24 in the direction perpendicular to the direction of linking of the curved parts 18a, 18b is made smaller than the width W of the line-shaped body 14, and in the present embodiment, the width w of the friable part 24 is made to be 0.2 to 0.5 times the width W of the line-shaped body 14. In addition, the thickness h of the friable part 24 is made thinner than the thickness H of the line-shaped body 14 at 0.2 to 0.5 times the thickness thereof.

Thus, by making the friable part 24 narrower and thinner than the line-shaped body 14, the cross sectional area of the friable part 24 (area of the cross section extending perpendicular to the direction of linking) is made smaller than that of the line-shaped body 14 (area of the cross section extending perpendicular to the length direction). The cross sectional area of the friable part 24 is preferably made 0.01 to 0.3 times as large as the cross sectional area of the line-shaped body 14.

Also, the connecting part 22 located at each end of the line-shaped body 14 in the length direction constitutes a linking part 26 without the friable part 24. This linking part 26 is, as shown in FIG. 1, provided for linking the curved parts 18a, 18b that are adjacent to each other in the axial direction, and these curved parts 18a, 18b are linked to each other by the linking part 26. In addition, the linking part 26 is made thicker than the friable part 24 at about the same thickness as the line-shaped body 14 as a part with high mechanical strength compared to the friable part 24. Also, the linking part 26 preferably is formed at each end of the line-shaped body 14 in the length direction in the number of about one to ten. The linking part 26 can be formed integrally with the line-shaped body 14 by laser processing or can be formed later by laser welding in the same manner as the friable part 24. Also, in the present embodiment, each end of the line-shaped body 14 in the length direction fog us a domain that goes one round around the circumference from each end of the line-shaped body 14, and a single linking part 26 is formed to link the curved part 18a or 18b located at the utmost end of the line-shaped body 14 to the curved part 18b or 18a adjacent thereto in the axial direction, respectively. However, each end of the line-shaped body 14 in the length direction whereby the linking part 26 is formed can be defined as a domain within a given range and should not be interpreted in a limited manner, which refers to, for example, a domain that covers an area of three rounds in the circumferential direction from each end of the line-shaped body 14. In other words, each end of the line-shaped body 14 in the length direction means the area in the line-shaped body 14 whereby the linking part 26 without the friable part 24 is formed.

The stent 10 with the connecting parts 22 described above are externally fitted onto an unillustrated balloon of a balloon catheter for stent expansion to be inserted into a stenosis portion of the somatic lumen. Then, by dilating the balloon of the balloon catheter for stent expansion, the stent 10 externally fitted onto the balloon undergoes a diameter enlarging deformation to get in close contact with the blood vessel wall. Thereafter, by means of withdrawing the balloon from the stent 10 by contracting the balloon, the stent 10 is implanted at the stenosis portion of the blood vessel, thus preventing the stenosis portion from restenosis.

During expansion of the stent 10 described above, the expanded stent 10 keeps some of the curved parts 18a, 18b adjacent to each other in the axial direction in linked conditions by the connecting parts 22, as shown in FIG. 6.

Furthermore, since the stent 10 has the line-shaped body 14 extending in a helical form in the circumferential direction while reciprocating in the axial direction at a given amplitude, the entire line-shaped body 14 undergoes deformation in a stable manner during expansion of the stent 10. In addition, since a plurality of connecting parts 22 are provided at equal intervals, a local increase in rigidity by formation of one of the connecting parts 22 causes no strain deformation in the stent 10. Therefore, the entire stent 10 undergoes a diameter enlarging deformation in a stable manner to get in full and close contact with the inner surface of the blood vessel, while avoiding problems such as partially pressing too hard thereon.

Also, because of the stress caused by pulsation of the blood vessel due to blood flow and curving movement of the blood vessel due to postural changes acting on the stent 10 implanted in the blood vessel, the friable parts 24 are ruptured to release the links made by the connecting parts 22 between the curved parts 18a, 18b adjacent to each other in the axial direction located in the middle section of the stent 10 (peripheral wail 12). This allows a relative displacement between the portions of the line-shaped body 14 adjacent to each other in the axial direction, that is, the line-shaped body 14 in a helical form alone is left in the middle of the peripheral wall 12 to make the stent 10 susceptible to curving deformation, thereby improving the pliability of the stent 10. As a result, the conformability of the stent 10 to the pulsation and curving of the blood vessel is enhanced to prevent stent fracture caused by implantation and the like of the stent at the curved part of the blood vessel so that a restrictive effect against restenosis can be expected. In addition, since the configuration conformability of the stent 10 is improved, during deformation of the blood vessel or during implantation of the stent 10 at the curved part of the blood vessel, the end tip of the axial direction of the stent 10 is prevented from being pressed hard on the blood vessel wall, thus preventing damage, infections and the like of the blood vessel caused by the abutment against the stent 10.

Since the main body of the stent 10 is composed of one line-shaped body 14 that extends in a helical form, in addition to the fact that it is possible to easily form the stent 10 with a few parts, the stent 10 does not get decomposed into multiple parts even if all the friable parts 24 rupture, thus effectively exerting the stent's intrinsic functions (e.g. maintaining the inner diameter of the blood vessel in an expanded state).

The friable part 24 can be made to rupture from fatigue failure by repeated action of stress caused by the pulsation of blood flow or the like, for example, or to rupture from shear failure by significant stress acting thereon caused by curving deformation of the blood vessel and the like. Furthermore, it may also be ruptured chemically through decomposition or degradation after implantation in the living body. In summary, the rupture mechanism of the friable part 24 is not particularly limited as long as the friable part 24 ruptures preferentially to the line-shaped body 14 by implantation of the stent 10 in the somatic lumen (e.g. blood vessel).

The rupture of the friable part 24 after implantation of the stent 10 as described above is achieved by making the cross sectional area of the friable part 24 smaller than that of the line-shaped body 14. In other words, when an external force caused by pulsation of blood vessel acts on the stent 10, concentrated stresses are applied to the friable part 24 with a smaller cross sectional area than the line-shaped body 14 so that the friable part 24 ruptures prior to the line-shaped body 14. Especially by setting the cross sectional area of the friable part 24 at 0.01 to 0.3 times the cross sectional area of the line-shaped body 14, the friable part 24 is maintained without rupture during expansion of the stent 10, while the friable part 24 is easily ruptured by implantation of the stent 10, thus maintaining the pliability of the stent 10.

Since the increase in the pliability of the stent 10 due to the rupture of the friable part 24 enhances the configuration conformability of the stent 10 to the deformation of the blood vessel caused by pulsation thereof and the like, the stress acting on the stent 10 becomes smaller than that prior to the rupture of the friable part 24, thereby leaving no chance of rupture for the line-shaped body 14 nor the linking part 26.

Meanwhile, at each end of the stent 10, the linking part 26 without the friable part 24 never ruptures even after implantation of the stent 10 in the blood vessel, keeping the curved parts 18a, 18b adjacent to each other in the axial direction in a linked state by the connecting part 22. This secures the configuration stability of the stent 10 to make it in close contact with the blood vessel walls at least at each end. As a result, shifting of the implant position of the stent 10 is prevented, thus stably maintaining the stenosis portion of the blood vessel in an expanded state. Since the cross sectional area of the linking part 26 is made larger than that of the friable part 24 to rupture the friable part 24 prior to the linking part 26 under the action of stress resulting in the lowered rigidity of the stent 10, the linking part 26 is maintained without rupturing under a condition of having the curved parts 18a, 18b linked to each other.

In addition, since each end of the line-shaped body 14 is widened to be the disc portion 20 in the stent 10 of the present embodiment, shifting of the implant position of the stent 10 is prevented more effectively by means of making the disc portion 20 in close contact with the blood vessel wall. Furthermore, since the wide disc portion 20 in a shape of a circular disc is provided at each end of the line-shaped body 14 in the stent 10 with a helical structure that turns out to be a free end, problems such as damaging the blood vessels by either end of the line-shaped body 14 stuck in the inner surface of the blood vessel can be avoided.

The disc portion 20 can also function as an angiographic marker when the stent 10 is implanted at the stenosis portion of the blood vessel. In other words, since the widened disc portion 20 with larger projected area than the line-shaped body 14 in the side and plan views is superior in visibility during angiography using X-rays and the like, provision of the disc portion 20 makes it easier to identify the location of each end of the stent 10. As a result, it is also made possible by angiography to more accurately determine whether the stent 10 is inserted in the intended site of implantation or whether the stent 10 is damaged or deformed and the like.

Figure 7:
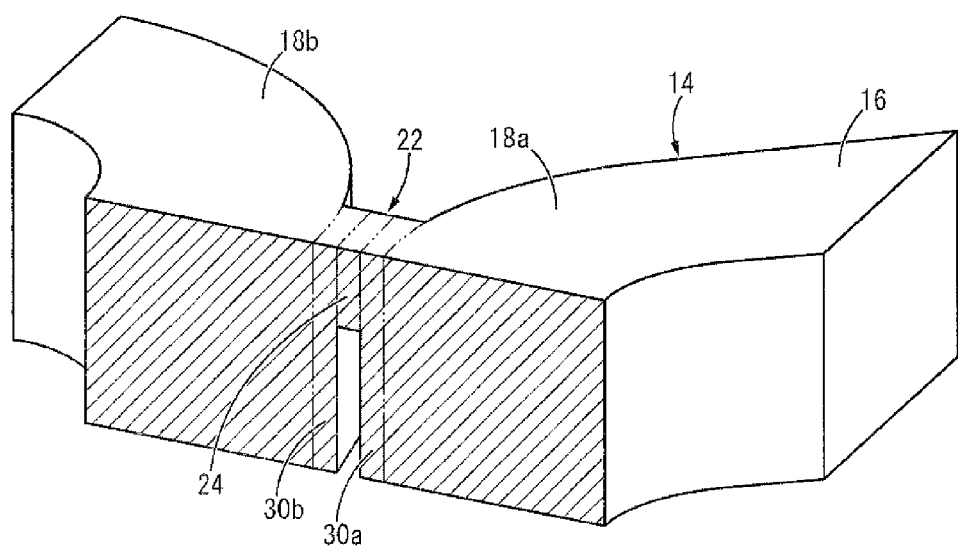
FIG. 7 is a cross sectional view showing a key portion of a stent as a second embodiment of the present invention.

FIG. 7 shows a key portion of the stent as a second embodiment of the present invention. In the following descriptions, substantially the same members and parts as those of the above-described first embodiment are omitted by assigning the same numerals to the equivalent components in each drawing. Also, the parts omitted from the drawings are identical to those of the first embodiment.

In other words, in the stent of the present embodiment, proximal protrusions 30a, 30b are provided on the parts adjacent to each other in the axial direction of the line-shaped body 14 (curved parts 18a, 18b adjacent to each other in the axial direction). The proximal protrusions 30a, 30b are protrusions protruding in the direction of facing of the curved parts 18a, 18b adjacent to each other in the axial direction between the opposing surfaces thereof, and are formed integrally with the respective curved parts 18a, 18b in the middle section in the length direction thereof. Namely, the curved part 18a is formed with a proximal protrusion 30a, while the curved part 18b adjacent to 18a in the axial direction is formed with a proximal protrusion 30b, and the protrusion tips of these proximal protrusions 30a, 30b are facing each other across a given distance in-between without touching. These proximal protrusions 30a, 30b are formed only at the intended site of the connecting part 22, which will be described later, and in the present embodiment, the proximal protrusion 30a is formed at every sixth of the plurality of curved parts 18a and the proximal protrusion 30b is formed at every sixth of the plurality of curved parts 18b, which are similarly arranged in a helical form in the circumferential direction.

Then, by irradiating laser beams at the protrusion tips of the proximal protrusions 30a, 30b to weld them to each other, the friable part 24 is formed between the protrusion tips of the proximal protrusions 30a, 30b that are linked to each other. This allows the connecting part 22 to be formed by including the proximal protrusions 30a, 30b and the friable part 24 in the middle section of the line-shaped body 14 in the length direction, and the curved parts 18a, 18b are linked to each other by the connecting part 22 restricting the relative displacement of adjacent parts in the axial direction of the line-shaped body 14. In FIG. 7, the borders between the line-shaped body 14 and the proximal protrusions 30a, 30b as well as the borders between the proximal protrusions 30a, 30b and the friable part 24 are each shown by two-dotted lines.

According to the stent of the present embodiment with the proximal protrusions 30a, 30b described above, the location of the friable part 24 formed by laser welding is easily identifiable, thus enabling to perform the forming work of the friable part 24 more easily and securely.

In addition, since the proximal protrusion 30a provided on the curved part 18a and the proximal protrusion 30b provided on the curved part 18b protrude in the direction of getting closer to each other, welding can be performed easily and securely between the proximal protrusions 30a, 30b to obtain the intended connecting part 22.

Figure 8:
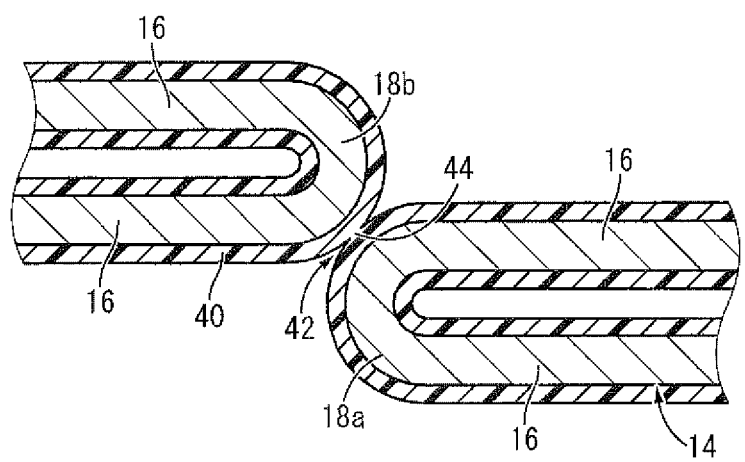
FIG. 8 is a cross sectional view showing a key portion of a stent as a third embodiment of the present invention.

FIG. 8 shows a key portion of the stent as a third embodiment of the present invention. That is, the stent of the present embodiment has the line-shaped body 14 with its surface covered by a coating layer 40 as an adherend. This coating layer 40 is formed with a biodegradable resin (such as polylactic acid, polycaprolactone or polyglycolic acid) and is deposited to cover the entire surface of the line-shaped body 14 made of a metal material.

Then, the portions of the coating layer 40 that cover the curved parts 18a and 18b of the line-shaped body 14 are adjacent to each other in the axial direction and are linked to each other by being integrated by laser welding. This causes a connecting part 42 to be formed at the portion of the coating layer 40 adhered by laser welding and the like, and the curved parts 18a and 18b adjacent to each other in the axial direction of the line-shaped body 14 are linked to each other by the connecting part 42 formed with the coating layer 40.

Also, by forming the coating layer 40 with biodegradable resin, the connecting part 42 is degraded and absorbed to rupture itself after implantation of the stent in the somatic lumen. This causes a friable part 44, which releases the linking of the line-shaped body 14 by the connecting part 42, to be formed with the coating layer 40.

The friable part 44 can be provided as part of the coating layer 40 that is integrally adhered to the line-shaped body 14 in a complex structure as in the case of the stent of the present embodiment. This allows the friable part 44 to be formed with materials with different rupture strength, biodegradability and in vivo degradation and so forth from those of the line-shaped body 14 or linking part 26, thereby causing rupture of the friable part 44 preferentially over other parts after implantation of the stent in the somatic lumen. Especially since the friable part 44 is provided by use of the coating layer 40 formed with a biodegradable resin, the rupture of the friable part 44 after implantation of the stent is stably caused by in vivo degradation.

In the present embodiment, the entire surface of the line-shaped body 14 is covered by the coating layer 40, part of which forms the friable part 44. However, for example, the adherend formed with a biodegradable resin can be adhered only to the curved part of the line-shaped body 14, all of which can form the friable part 44. Also, the connecting part having the friable part can be formed with the adherend by means of adhering later the adherend formed separately from the line-shaped body 14.

Figure 9:
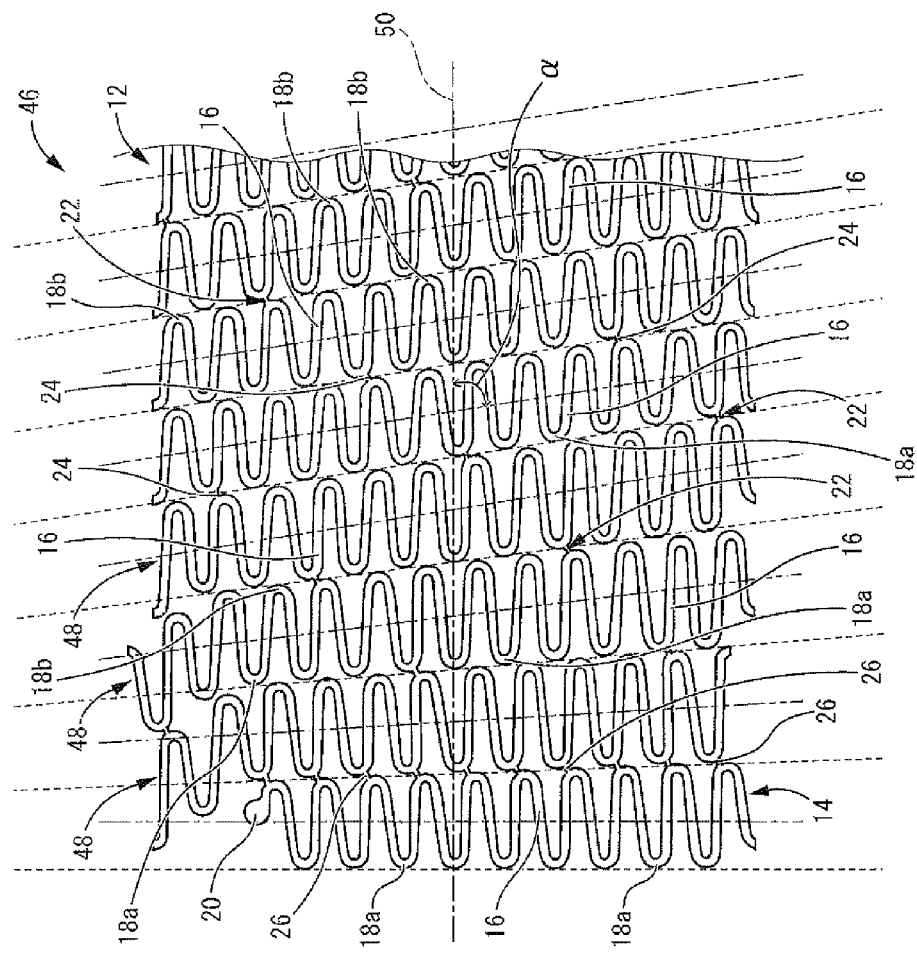
FIG. 9 is a developed view of a stent as a fourth embodiment of the present invention obtained by cutting the stent along a line on a circumference.

FIG. 9 shows a stent 46 as a fourth embodiment of the present invention. The stent 46 of the present embodiment has basically the same shape as that of the stent 10 of the first embodiment described above, and a developed view obtained by cutting the stent 46 along a line on the circumference is shown in FIG. 9. Also, in FIG. 9, one end of the stent 46 is shown, and the other end is omitted because of its approximate rotational symmetry with the shape in FIG. 9.

In other words, in the first embodiment described above, each end surface of the stent 10 in the axial direction is on a plane tilted against the axial direction, but in the present embodiment, each end surface of the stent 46 in the axial direction is on a plane nearly perpendicular to the axial direction. Namely, the position of each line-shaped body 14, that is, curved part 18a or 18b is substantially lined up at each end of the stent 46 in the axial direction. Also, in the stent 10 of the first embodiment described above, the line-shaped body 14 extends in a helical form in the circumferential direction reciprocating in the axial direction at a nearly constant amplitude over the entire length thereof, whereas in the stent 46 of the present embodiment, the reciprocation amplitude of the line-shaped body 14 in the axial direction gradually changes at each end of the stent 46 in the axial direction. The structure of the stent 46 in the middle section in the axial direction is equivalent to that of the first embodiment described above.

More specifically, in each end of the stent 46 in the axial direction, at one location along the circumference of the line-shaped body 14, a widened portion 48 is provided with its amplitude made larger than those of other portions along the circumference. In FIG. 9, the widened portion 48 is shown at the top of the stent 46.

Under these circumstances, the dash lines in FIG. 9 show both ends of the width direction of the reciprocation amplitude of portions other than the widened portion 48. In other words, the dash lines in FIG. 9 show straight lines connecting adjacent curved parts 18a, 18a or 18b, 18b at locations other than the widened portion 48 of the line-shaped body 14. As shown in FIG. 9, the size of the amplitude of the widened portion 48 exceeds the separation distance between the dash lines, and in the stent 46, the angle α of the helix that continues to extend from each end of the widened portion 48 is varied thereby.

The reciprocation amplitude of the line-shaped body 14 of the present embodiment is made nearly the same as that of the stent 46 in the middle section in the axial direction even at the shortest portion located at the end of the stent 46 in the axial direction. Especially in the present embodiment, the reciprocation amplitude of the line-shaped body 14 particularly changes at the widened portion 48, and the difference between the longest and shortest sizes of the reciprocation amplitude of the line-shaped body 14 of the stent 46 is set at 0.5 mm or smaller.

The helical inclination angles relative to the axial direction of the line-shaped body 14 are made nearly equal to each other over the entire length thereof in the stent 10 of the first embodiment described above, but in the stent 46 of the present embodiment, by use of the widened portion 48 described above, the helical inclination angle relative to the axial direction of the line-shaped body 14 is made to change gradually. More specifically, the helical inclination angle of the line-shaped body 14 relative to the axial direction gradually increases toward each end of the stent 46 in the axial direction, getting closer to the vertical (90 degrees). Especially in the present embodiment, the helical inclination angle of the line-shaped body 14 is made almost vertical around the end tip of the stent 46 in the axial direction.

However, the helical inclination angle of the line-shaped body 14 does not have to reach the vertical at the end tip of the stent 46 in the axial direction and can also reach an inclination angle slightly exceeding the vertical. Preferably, the helical inclination angle of the line-shaped body 14 reaches at least 80 degrees at the end tip of the stent 46 in the axial direction, and more preferably, the angle is set in the range of 85 to 90 degrees. In general, the inclination angle of the middle section of the stent 46 is preferably set in the range of 50 to 75 degrees. Also, the range of variation wherein the helical inclination angle of the line-shaped body 14 gradually changes, that is, the setting range of the widened portion 48 can be no less than one round in the circumferential direction of the stent 46, but preferably set at no less than two rounds, and more preferably set to vary in no less than three rounds. This makes it possible to avoid a rapid change of the helical inclination angle of the line-shaped body 14, thus causing smoother deformation and expansion of the stent 46 over the entire length thereof by means of setting the variation in the inclination angle per one round at 5 degrees or less.

The helical inclination refers to the angle of the helix shown by two-dotted lines in FIG. 9 that connect the center point of each linear part 16 of the line-shaped body 14 adjacent to each other in the middle section in the axis-perpendicular direction (up-down direction) in FIG. 9, and is represented by the value of "90 degrees minus lead angle." In FIG. 9, the inclination angle of the helix is indicated as an angle α relative to a central axis 50 that extends in the axial direction shown by the one-dotted line (left-right direction in FIG. 9).

In the stent 46 of the present embodiment with the structure described above, each end surface of the stent 46 is made nearly perpendicular to the axial direction, and the positions of the curved parts 18*a*, 18*b* of the line-shaped body 14 are almost lined up at both ends so that the tip end of the stent 46 in the axial direction can be effectively prevented from floating up locally when the stent 46 passes through a bent portion of the blood vessel. In addition, because the inclination relative to the axial direction is made at a right angle by providing the widened portion 48 at each end of the line-shaped body 14 to vary the reciprocation amplitude, expansion and flexion of the stent 46 can be performed effectively. In other words, by providing the widened portion 48, the inclination angle at each end of the stent does not change rapidly, that is, there is no need for providing any portion with an excessively long or excessively short amplitude in the line-shaped body 14. This allows the stent 46 of the present embodiment to exert favorable effects of expansion and flexion. Namely, if a portion with an excessively short amplitude is provided at the end of the stent, there is a risk of having difficulties in obtaining an expanding effect at the end equivalent to that of the middle section. Also, if a portion with an excessively long amplitude is provided at the end of the stent, the flexibility is lowered posing a risk of having difficulties in achieving smooth deformation and expansion over the entire length of the stent 46.

Embodiments of the present invention have been described in detail above, but the present invention is not limited by those specific descriptions. For example, in some of the embodiments described above, an example where the friable part 24 is formed by laser welding of the line-shaped body 14 is shown, but the friable part can also be formed integrally with the line-shaped body 14 in a similar way of cut-out thereto when the line-shaped body 14 is cut out by laser from a cylindrical metal member. According to this method, there is no need for post-processing such as laser welding in order to form the friable part, thereby reducing the number of manufacturing processes. In case of forming the friable part integrally with the line-shaped body 14, the cross sectional area of the connecting part is made smaller than that of the line-shaped body 14, which causes preferential rupture of the connecting part over other parts.

Also, the friable part is not necessarily limited to the one formed with metal materials, but for example, can be formed with a synthetic resin material having biodegradability (which is degraded and discharged or absorbed in the somatic lumen after implantation of the stent) or with a bonding agent and the like. Thus, in cases where the friable part is formed with a material different from that of the line-shaped body 14, it is not essential that the cross sectional area of the friable part be smaller than that of the line-shaped body 14. In other words, as long as the friable part is formed with a material with lower strength (more susceptible to rupturing with the same shape) or a material easier to decompose or erode in the living body than that of the line-shaped body 14 so that the friable part ruptures before the line-shaped body 14 under the implanted condition, the cross section of the friable part can be made the same as or larger than that of the line-shaped body 14. In summary, in the present invention, it is necessary for the friable part to rupture preferentially over the line-shaped body under the implanted condition, but it does not matter whether such a preferential rupturing of the friable part is caused by differences in shape and size (cross sectional area) or a difference in material between the friable part and the line-shaped body.

Also, the rupture timing of the friable part 24 can be after the implantation of the stent 10 in the somatic lumen (e.g. blood vessel) or can be at the time of expansion (during and upon completion of expansion) of the stent 10. The rupture timing of the friable part 24 can be controlled by means of adjusting the diameter enlargement rate (ratio of diameter after expansion to diameter before expansion) of the stent 10 as well as adjusting the shape and size of the friable part 24.

Also, the friable part 24 to be formed can be set in any number. Furthermore, the friable part 24 does not necessarily have to be formed at every sixth of the plurality of curved parts 18*a* but can be formed at any interval or at every curved part 18*a*. Moreover, it is desirable that the friable part 24 be foamed at equal intervals in the line-shaped body 14 in order to secure the configuration stability of the stent 10 during expansion, but in cases where the line-shaped body is in an uneven shape in the length direction, for example, the configuration stability can be rather enhanced by means of forming the friable part at unequal intervals.

Also, the number of linking parts to be formed is not particularly limited as long as they are provided at both ends of the line-shaped body 14, and one or more, or even none of them can be formed. Furthermore, like the connecting parts, the linking parts can be provided later by welding or adhesion of other members formed with synthetic resin and the like, in addition to being formed integrally with the line-shaped body 14.

Also, in some of the embodiments described above, the connecting part 22 is formed to link the curved parts 18*a* and 18*b* arranged adjacent to each other at the closest locations in the axial direction, but the formation locations of the connecting parts are not particularly limited as long as they are provided to have the adjacent segments in the axial direction linked to each other in the line-shaped body. More specifically, the connecting parts can be provided so as to link the linear parts 16, 16 of the line-shaped body 14 adjacent to each other in the axial direction, or to link the linear part 16 and the curved part 18*a*/18*b* to each other. Furthermore, the connecting parts can be provided to link the curved parts 18*a* and 18*b* arranged far separated from each other in the axial direction.

Also, the line-shaped body 14 of the embodiments described above has a structure where the linear part 16 and the curved part 18*a*/18*b* are provided alternately in a continuous manner to extend in a helical form in the circumferential direction while reciprocating in the axial direction, but the shape of the line-shaped body is not limited to the one described in the embodiments described above. In other words, the line-shaped body can extend in a helical form in the circumferential direction while curving in waves (e.g. sine curve), for example, over the entire length thereof, whereas the ones with linear configuration that extend in a helical form in the circumferential direction while turning in zigzags and reciprocating in the axial direction can also be adopted.

Furthermore, the line-shaped body can be obtained by processing wires into a configuration that extend in a helical form in the circumferential direction while reciprocating in the axial direction, in addition to being formed by cutting out a cylindrical metal material by laser processing.

Also, the scope of application of the present invention is not limited to stents to be expanded by a balloon (balloon expandable stents), but it is applicable to those with a self-expansion function (self-expandable stents) by forming the stents with materials that exert a shape-memory effect such as Ni—Ti alloy, for example. More specifically, a stent that memorizes an expanded state, for example, can recover its original expanded state based on the shape-memory effect after insertion into the protection sheath in a contracted state to be constrained therein, while constraints against the stent by the protection sheath is released by removing the protection sheath from the stent at the implant position in the somatic lumen. Even this type of stent with a self-expansion function can achieve configuration stability in an expanded state as well as pliability in an implanted state by the provision of the connecting parts 22 linking the line-shaped body 14.

Moreover, in the fourth embodiment described above, the widened portion 48 is provided at one location on the circumference, but it can be provided at multiple locations along the circumference. Also in the fourth embodiment described above, the helical inclination of the stent 46 is varied by providing a stepped-variable portion in the axial direction such as the widened portion 48, but it is not limited to such a configuration. For example, the helical inclination can be varied by changing the reciprocation amplitude of the line-shaped body 14 gradually at an approximately constant rate. In such a configuration as well, the uniform expansion effect of the stent can be exerted sufficiently. Also, in this case, the reciprocation amplitude can be changed gradually from the middle section toward each end, or can be changed at each end, for example, within a range up to the four rounds in the circumferential direction of the stent.

| KEYS TO SYMBOLS | | |
| --- | --- | --- |
| 10, 46: Stent, | 12: Peripheral wall, | 14: Line-shaped body, |
| 18: Curved part (adjacent portions in the axial direction of the line-shaped body), | | |
| 20: Disc portion, | 22, 42: Connection part, | 24, 44: Friable part, |
| 26: Linking part (connecting part located at each end of the line-shaped body in the length direction), | | |
| | 30: Proximal protrusion, | 40: Coating layer (adherend) |

The invention claimed is:

1. A stent configured for insertion into a somatic lumen, comprising:
a cylindrical peripheral wall formed with a line-shaped body that extends in a helical form in a circumferential direction while reciprocating in an axial direction at a given amplitude,
the line-shaped body including linear parts, which extend in the axial direction for a given length, and curved parts, which curve approximately in a semi-circular shape, the linear parts and the curved parts alternating in a continuous manner; and
a plurality of connecting parts such that each connecting part links adjacent curved parts of the line-shaped body in the axial direction,
the plurality of connecting parts including first connecting parts and second connecting parts,
the first connecting parts being located in a middle section of the line-shaped body in a length direction, the first connecting parts each including a friable part that has a smaller mechanical strength than a mechanical strength of the line-shaped body, and the stent has the first connecting part each including the friable part when being inserted into the somatic lumen so that the friable part is configured to rupture and release a link made by the first connecting part due to stress cause by deformation of the somatic lumen, and
the second connecting parts being located at both ends of the line-shaped body in the length direction, the second connecting parts provide at a location so as to link ones of the curved parts that are adjacent in the axial direction,
wherein the adjacent curved parts are shifted from each other in the circumferential direction so that a center axis of a fist curved part is offset from a center axis of a second adjacent curved part and is offset from each of the plurality of connecting parts.

2. The stent according to claim 1, wherein the friable part is formed of a cross sectional area, extending perpendicular to a direction of linking of the first the connecting part, smaller than that extending perpendicular to a length direction of the line-shaped body.

3. The stent according to claim 1, wherein a reciprocation amplitude of the line-shaped body in the axial direction is approximately constant over an entire length of the line-shaped body.

4. The stent according to claim 1, wherein a helical inclination angle of the line-shaped body relative to the axial direction gradually increases toward each end of the stent.

5. The stent according to claim 1, wherein the plurality of connecting parts are provided at a constant interval.

6. A method of manufacturing a stent according to claim 1, wherein the friable part is formed by having the adjacent curved parts welded to each other by laser.

7. The method of manufacturing the stent according to claim 6, wherein proximal protrusions are disposed on the adjacent curved pats in the axial direction where the friable part is formed by welding the proximal protrusions to each other by laser.

8. The stent according to claim 1, wherein each end of the line-shaped body in a length direction includes a widened disc portion.

9. The stent according to claim 1, wherein the friable part includes an adherend that is made of a different material than the line-shaped body and that is adhered to the line-shaped body.

10. The stent according to claim 9, wherein the adherend is formed of a biodegradable resin.

11. The stent according to claim 1, wherein:
the first connecting parts are located only in the middle section of the line-shaped body in the length direction, and
the second connecting parts are located only at both ends of the line-shaped body in the length direction.

12. The stent according to claim 1, wherein the friable part has a width that is 0.2 to 0.5 times a width of the line-shaped body, and has a thickness that is 0.2 to 0.5 times a thickness of the line-shaped body.

13. A stent configured for insertion into a somatic lumen, comprising:
a cylindrical peripheral wall formed with a line-shaped body that extends in a helical form in a circumferential direction while reciprocating in an axial direction at a given amplitude, the line-shaped body including linear parts, which extend in the axial direction for a given length, and curved parts, which curve approximately in a semi-circular shape, the linear parts and the curved parts alternating in a continuous manner; and a plurality of connecting parts such that each connecting part links adjacent curved parts of the line-shaped body in the axial direction, wherein the plurality of connecting parts each include a friable part that has a smaller mechanical strength than a mechanical strength of the line-shaped body so that the friable part is configured to rupture and release a link made by the connecting part due to stress caused by deformation of the somatic lumen, and wherein the adjacent curved parts are shifted from each other in the circumferential direction so that a center axis of first curved part of the curved parts is offset from a center axis of an adjacent second curved part of the curved pats and is offset from each of the plurality of connecting parts.

14. The stent according to claim 13, wherein the reciprocation amplitude of the line-shaped body in the axial direction is approximately constant over an entire length of the line-shaped body.

15. The stent according to claim 13, wherein a helical inclination angle of the line-shaped body relative to the axial direction gradually increases toward each end of the stent.

16. A method of manufacturing a stent according to claim 13, wherein the friable part is formed by having the adjacent curved parts welded to each other by laser.

17. The method of manufacturing the stent according to claim 16, wherein proximal protrusions are disposed on the adjacent curved parts in the axial direction where the friable part is formed by welding the proximal protrusions to each other by laser.

18. The stent according to claim 13, wherein each end of the line-shaped body in a length direction includes a widened disc portion.

19. The stent according to claim 13, wherein the friable part includes an adhered that is made of a different material than the line-shaped body and that is adhered to the line-shaped body.

20. The stent according to claim 19, wherein the adherend is formed of a biodegradable resin.

* * * * *